United States Patent [19]
Rosen et al.

[11] Patent Number: 5,425,735
[45] Date of Patent: Jun. 20, 1995

[54] SHIELDED TIP CATHETER FOR LITHOTRIPSY

[75] Inventors: David I. Rosen, Peabody; Charles Shibilia, Westford, both of Mass.

[73] Assignee: PSI Medical Products, Inc., Norwalk, Conn.

[21] Appl. No.: 129,554

[22] Filed: Sep. 22, 1993

Related U.S. Application Data

[63] Continuation of Ser. No. 808,527, Dec. 16, 1991, abandoned, which is a continuation-in-part of Ser. No. 632,487, Feb. 4, 1991, abandoned, which is a continuation of Ser. No. 314,472, Feb. 22, 1989, abandoned.

[51] Int. Cl.⁶ ............................................. A61B 17/00
[52] U.S. Cl. ................................. 606/128; 606/2.5; 604/164
[58] Field of Search ............... 606/2, 2.5, 127, 128; 128/7; 604/130, 134, 135, 140, 141, 143, 144, 157, 164, 170

[56] References Cited

U.S. PATENT DOCUMENTS

| | | |
|---|---|---|
| 3,785,382 | 1/1974 | Schmidt-Kloiber et al. |
| 3,823,717 | 7/1974 | Pohlman et al. |
| 3,927,675 | 12/1975 | Pohlman et al. |
| 4,191,189 | 3/1980 | Barkan . |
| 4,196,736 | 4/1980 | Watanabe . |
| 4,227,532 | 10/1980 | Bluhm et al. |
| 4,548,207 | 10/1985 | Reimels ............................ 606/50 |
| 4,605,003 | 8/1986 | Oinuma et al. |
| 4,624,253 | 11/1986 | Burns ............................... 606/181 |
| 4,639,252 | 1/1987 | Kelly et al. |
| 4,686,980 | 8/1987 | Williams et al. ................. 606/50 |
| 4,687,471 | 8/1987 | Twardowski et al. |
| 4,722,340 | 2/1988 | Takayama et al. |
| 4,870,953 | 10/1989 | DonMicheal et al. |
| 4,927,426 | 5/1990 | Dretler . |
| 4,927,427 | 5/1990 | Kriauciunas et al. |
| 4,932,954 | 6/1990 | Wondrazek et al. |
| 4,983,877 | 1/1991 | Kashiwara et al. ............... 313/140 |

FOREIGN PATENT DOCUMENTS

| | | |
|---|---|---|
| 801472 | 12/1968 | Canada . |
| 317507 | 5/1989 | European Pat. Off. |
| 3707567 | 9/1987 | Germany . |
| WO91/10403 | 7/1991 | WIPO . |

OTHER PUBLICATIONS

Bhatta, et al., *J. Urology*, 142: 1110 (1989) "In Vitro Studies of Plasma Shield LaserTripsy".
Bhatta, et al. *J. Endourology*, 3(4): 433–437 (1989) "Shielded Electrohydraulic Lithotripsy of Urinary etc."
Bhatta, et al. *J. Urology*, 143: 857–860 "Effects of Shielded of Unshielded Laser "...
Nishioka et al., *Lasers In the Life Sciences*, 1(3): pp. 231–245 (1987), "Mechanism of Laser-Induced Fragmentation"...
Dretler et al., *J. Urology*, 146: 746–750 (Sep. 1991), Conversion of the Electrohydraulic Electrode ... Case Report.
Fair, Harry D., Jr., *In Vitro Destruction of Urinary Calculi by Laser-Induced Stress Waves*, vol. 12, No. 2, Mar.-Apr. 1978.
Thomas et al., "The Development of an Endoscopically Applicable Optomechanical Coupler for Laser-Induced Shock Wave Lithotrispy (LISL)," Ulm Germany, 1987.

*Primary Examiner*—Stephen C. Pellegrino
*Assistant Examiner*—Jeffrey A. Schmidt
*Attorney, Agent, or Firm*—Kenyon & Kenyon

[57] ABSTRACT

A shielded tip catheter for use with a pulsed energy source for fracturing deposits such as urinary and biliary stones and atherosclerotic plaque in the human body is disclosed. The flexible catheter has a shielded tip structure which is adapted for insertion through a fluid passage in a living body. The tip structure can contain an impact element, a scraping implement or a cutting implement. An energy source creates repeated rapid vapor expansions adjacent the element causing it to undergo repeated pulse like movements, imparting a series of high-velocity impulses to an adjacent deposit, thereby fracturing or cutting it. The energy source can be a laser with a fiber optic delivery system in the catheter terminating adjacent the impact element, or a spark generator with a conductor within the catheter to deliver a fluid vaporizing spark adjacent the element.

28 Claims, 3 Drawing Sheets

SHIELDED TIP CATHETER FOR LITHOTRIPSY

RELATED APPLICATIONS

This application is a continuation of application Ser. No. 07/808,527, now abandoned, filed Dec. 16, 1991, entitled SHIELDED TIP CATHETER, which is a continuation-in-part of U.S. application Ser. No. 07/632,487, filed Feb. 4, 1991, now abandoned, which is a continuation of U.S. Ser. No. 07/314,472, filed Feb. 22, 1989, now abandoned, the entire disclosures of which are hereby incorporated herein by reference.

BACKGROUND OF THE INVENTION

Calciferous and similar deposits occur in body fluid passages of various types, including kidney stones, gall stones, and arterial plaque. Surgery or radiation typically has been used for removing or destroying such deposits. In one form of laser therapy, radiation is directed onto a light-receiving surface of a heat-generating element. The element is then placed in contact with the target deposit, melting it. This approach has several drawbacks which include, for example, thermal damage to surrounding tissue, formation of char and debris from advanced fibrous and calcified plaques, and adhesion of the hot element to the tissue thereby rupturing it when the element is removed.

In another approach, known as direct lasertripsy, laser radiation is applied directly to the target deposit to ablate it or produce shock waves that induce fragmentation. Direct lasertripsy also has several disadvantages. For example, laser energy often damages healthy tissue surrounding the target deposit by direct absorption or by acting as a general heat sink for the high temperature plasma. Some deposits only weakly absorb radiation which requires the use of higher levels of radiation and consequent tissue damage.

Impact lithotripsy has been used for treating some hard deposits. For example, Pohlman et al. in U.S. Pat. No. 3,927,675 describe a device for fragmenting hard deposits in the urinary tract using ultrasonic energy. This device has several drawbacks, including the use of a thick spiral metal probe within the catheter, and it requires that ultrasonic energy be transmitted the length of the catheter which causes vibration along the length of the catheter. In U.S. Pat. No. 3,823,717, Pohlman et al. describe another ultrasonic device having an implement with a cutting edge attached to the end of the catheter. This device suffers all the drawbacks of the other Pohlman device with the additional disadvantage that the cutting edge appears to be exposed, which could damage surrounding tissues.

Oinuma et al. in U.S. Pat. No. 4,605,003 describe a lithotripter which utilizes a gas-generating explosive to drive an impact element against a stone in a body. This device is capable of only a single pulse, which exhausts the explosive. Thus, if the impact misses the target or fails to break it, the catheter must be withdrawn, the explosive recharged and the catheter reinserted for each additional attempt.

Schmidt-Kloiber et al. in U.S. Pat. No. 3,785,382 describe a lithotripter which utilizes a driving mechanism based on a water-filled chamber in which a hydraulic wave is induced by electrodes and transmitted through a membrane to the lithotripter wire which is threaded into the body. The design of this device requires that the mechanical energy resulting from the hydraulic wave be transmitted over the length of the lithotripter wire, so that if the wire takes one or more turns in a convoluted body passage, much of the energy could be transmitted to healthy tissue before it reaches the stone.

It is an object of the present invention to provide a safe, effective catheter design which is free of these and other disadvantages.

SUMMARY OF THE INVENTION

The present invention relates to a catheter for use with a pulsed energy source for selectively removing hard or soft deposits in body passages. The catheter is equipped with a tip structure which contains an impact element for fracturing hard deposits, such as kidney stones, or cutting or scraping implements for removing soft deposits, such as arterial plaque.

In one embodiment, the catheter comprises an elongate member terminating in a tip structure which contains an impact element and means for operating it. The tip structure in this embodiment contains a housing defining a distal end which encloses a spring stop and an impervious shield region surrounding a pair of electrodes. The electrodes comprise the terminal end of two insulated wires which run from a power source through the length of the catheter, and are spaced apart to form a spark gap. The distal end of the housing further contains the impact element, which is preferably a piston-shaped probe having an impact end, a driving surface and a shoulder region. The impact element is adapted for axial reciprocating movement in which pressure on the driving surface causes the probe to move forward such that the impact end extends beyond the housing and collides with the target deposit. The forward movement of the probe is limited by the shoulders, which are prevented by the spring stop from progressing beyond a certain point. A spring disposed within the housing between the shoulder and the spring stop returns the impact element to its original position.

In another embodiment, a scraping implement is used in lieu of the impact element. The scraping implement preferably has a knife edge which is aligned with the distal end of the housing, a driving surface for propelling the knife edge beyond the housing and shoulders for preventing the implement from leaving the housing. The scraping implement works like the impact element in that it is capable of axial reciprocating motion which allows it to be used to scrape or cut away arterial plaque, for example.

In another embodiment, a blade can be used as a cutting implement. The cutting implement has blades which can be used to cut hard or soft deposits in body passages, a driving surface and shoulders for preventing the implement from leaving the housing. Like the impact and scraping implements, the cutting implement is capable of axial reciprocating motion.

In another embodiment, the impact element can be a wedge-shaped tip. The wedge is used like the impact element to strike a deposit in a body passage with repeated impacts to fragment or break apart the deposit. In implementing the invention, a flexible catheter terminating in the tip structure is inserted through a body passage until the tip structure is adjacent the deposit of interest. The other end of the catheter is attached to an energy source. The energy source provides a pulse of energy which is transmitted through the conduits in the catheter to the tip structure. Fluid is admitted into the housing through the catheter or through ports in the housing. The pulse of energy vaporizes the fluid and causes the impact or cutting element to undergo a pulse like movement as the vapor expands against the driving surface, thereby imparting a high-velocity impulse to the target deposit. This motion can be repeated by applying a series of energy pulses to the electrodes, causing repeated vaporization of fluid and driving the impact or cutting element to repeated impacts with the deposit. A compressable spring causes the element to return to its original position after each pulse.

The energy source can be a pulsed laser which is delivered through an optical fiber passing through the catheter to terminate adjacent to the driving surface, or can be a pulsed voltage source which delivers a spark through the pair of insulated conductors to electrodes within the housing.

The present catheter has several advantages. It has a narrower diameter than currently available catheters, which allows it to be inserted into smaller passageways. The housing encloses all of the cutting or impact implements and the spark or laser, which increases patient safety and protects healthy tissue from direct laser radiation or thermal radiation from the vapor expansion which forms against the inside surface of the housing.

DESCRIPTION OF THE FIGURES

The foregoing summary of the invention and various features thereof, as well as the invention itself, may be more fully understood from the following description, when read together with the accompanying drawings.

DETAILED DESCRIPTION OF THE INVENTION

The present invention is directed to an improved catheter for use in lasertripsy or lithotripsy. The present device will be described herein with particular reference to impact lithotripsy, however, the general principles apply to other procedures.

Figure 1:
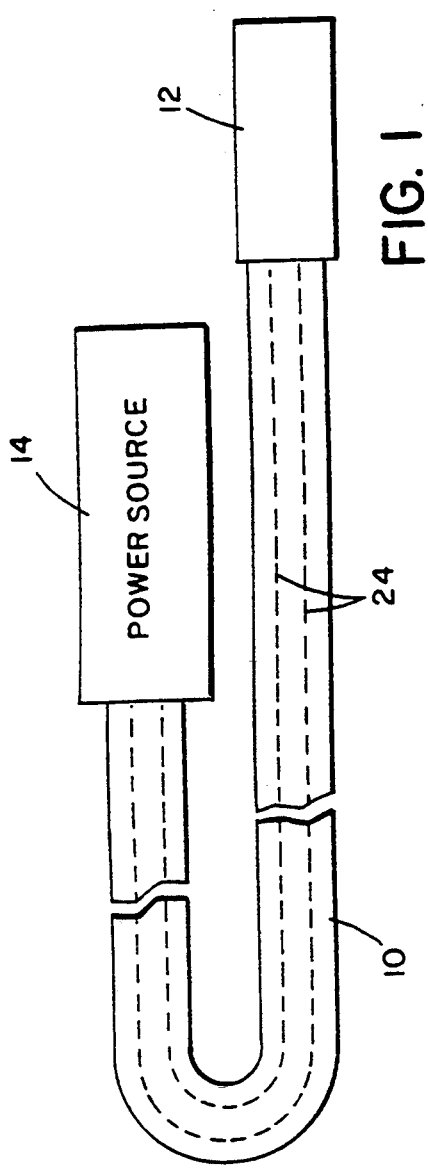
FIG. 1 is a schematic illustration of one embodiment of the invention showing a power source and a catheter with a shielded tip.

A general embodiment of the invention is illustrated in FIG. 1, which shows a flexible catheter 10 terminating in a tip structure 12. The catheter 10 generally comprises a commercially available extruded catheter which can have an outer diameter of from about 1 mm to about 2 mm, preferably about 5 french (1.6 mm). The tip 12 is typically fabricated from stainless steel or other metal. The catheter is adapted for connection to a power source 14, which provides an energy pulse which is transmitted to the tip structure through conduits 24.

The power source 14 can be a laser system or a spark generator. Laser systems which are useful for this purpose include, for example, tunable dye lasers. The laser is operated in the mode of producing repeated pulses of approximately 1 microsecond duration and approximately 50 millijoules of energy. Other pulsed laser systems which are capable of creating a plasma and are compatible with optical fiber transmission would also be acceptable energy sources. These include, for example, solid state laser systems such as Alexandrite. Spark generators which can be used include, for example, a Wolfe 2137.50 or Northgate Research SD1. The spark generator preferably produces repeated output pulses of up to several microseconds, at several KV and up to about 1 KA current.

Figure 2A:
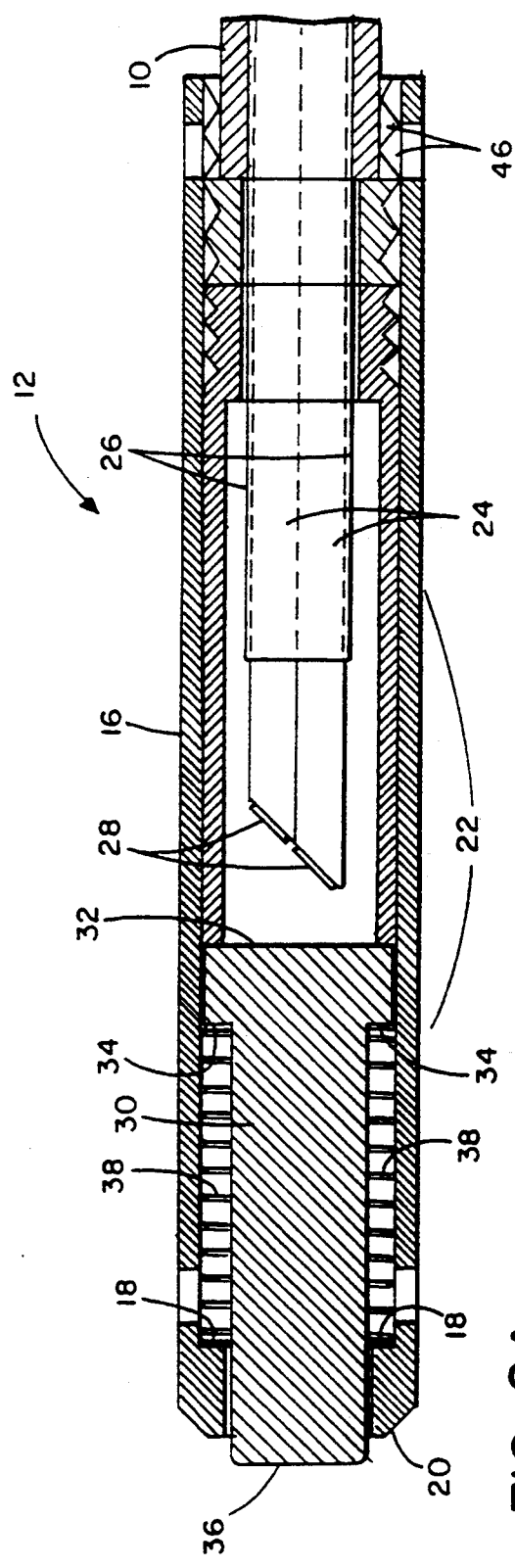
FIG. 2A is a cross-sectional view of the tip structure of the device of FIG. 1, wherein an impact element is in a first position.
Figure 2B:
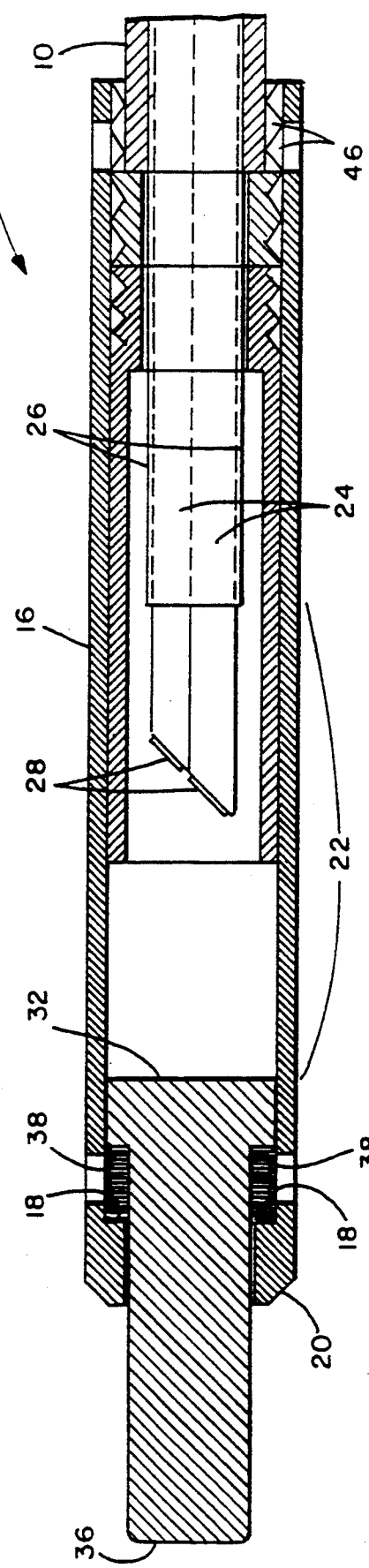
FIG. 2B is a cross-sectional view of the tip structure of the device of FIG. 1, wherein the impact element is in a second position.

A more detailed view of the tip structure is shown in FIGS. 2A and 2B. As shown in the figures, the tip structure 12 comprises a housing 16 having a distal end 20, and an impervious shield region 22. The distal end 20 defines a spring stop 18 in the interior of the housing. The housing 16 surrounds a pair of electrodes 28 which are powered through insulated wires 24. A piston shaped impact element 30 is disposed within the housing 16. The piston comprises an impact end 36, a driving surface 32 and shoulders 34. The piston 30 is adapted for axially reciprocating movement within the housing. FIG. 2B shows the impact element 30 in its extended position. As shown, spring 38 is compressed between spring stop 18 and shoulder 34 when the piston element is extended. The tip structure 12 is attached to catheter 10, preferably by mating threaded areas 46.

Figure 3:
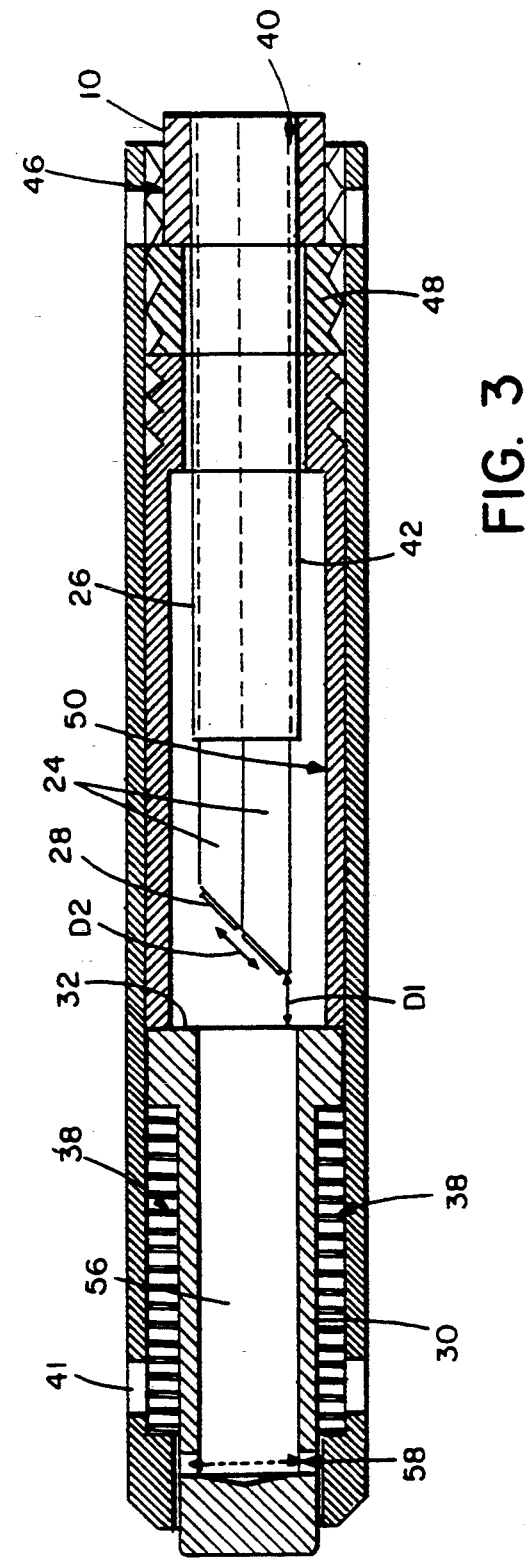
FIG. 3 is a schematic exploded cross-sectional view of the tip structure.

A preferred embodiment of the tip structure is illustrated in FIG. 3. In this embodiment, catheter 10 has a tip structure 12 releasably attached to one end, preferably by screwing together threaded areas 46. Insulated wires 24 pass centrally through the catheter 10 terminating at a point adjacent the driving surface 32 of piston 30. The distance between the end of electrodes 28 and the driving surface 32 is distance D1. Distance D1 represents an optimum power distance, which is important to the proper operation of the device. If the distance D1 is too close, the spark could short to the piston 30 and fail to provide the vaporization energy needed to drive the piston. That is, the electrical spark emitted from the electrodes would jump to the piston 30 rather than and be conducted and dissipated along piston 30 rather than providing the energy of vaporization needed to vaporize the fluid to drive the piston forward. If the distance D1 is too far, the energy transfer from the vaporization to the piston is less effective. Distance D1 can be from about 0.030 inches to 0.080 inches. The preferred distance D1 is about 0.040 inches ±0.010 inches. The insulated wires 24 terminate in electrodes 28 which define a spark gap having a distance D2. The spark gap distance D2 is selected to provide, in response to energization from a spark generator, a vaporization of the fluid within the housing 16 generating a pulse motion of the piston 30. Distance D2 can be from about 0.010 to about 0.030 inches. The preferred spark gap distance D2 is about 0.015 inches to about 0.030 inches.

In the preferred embodiment of the present invention shown in FIG. 3, the distal end of housing 16 and the impact end of probe 30 are rounded to minimize trauma to tissues when the catheter is inserted into a body passage. Spring means 38 is preferably a compression spring. A single spring which encompasses or surrounds piston 30 can be used, or a plurality of springs located between the piston 30 and the interior wall of housing 16. Housing 16 is preferably fabricated from a high tensile strength metal, such as stainless steel, titanium, or nickel-based alloys, such as Inconel TM. The piston 30 also preferably is fabricated from a metal, such as stainless steel, however any hard impact resistant material can be used. Piston 30 may have a central lumen 56 and ports 58 if desired, to permit the passage of fluid through the piston. Ports 44 preferably are included near the distal end 20 of housing 16 to permit the expulsion of excess fluid around the spring 38 during compression by the tip.

In a particularly preferred embodiment, electrodes 28 are chamfered at an acute angle as shown in FIGS. 2 and 3. Chamfering the electrodes provides an increased spark gap (distance D2) for more spark energy without increasing the diameter of the wires. This allows distance D2 to be varied without changing distance D1, and permits narrower conduits, and consequently a narrower gauge catheter, to be used. Narrower catheter diameter, in turn, allows the catheter to be used in smaller body passages.

The conduits 24 can be insulated wires, where the power source is a spark generator, or can be optical fibers, where the power source is a laser. In a currently preferred embodiment, the catheter is used with a spark generator, and the conduits 24 comprise insulated wires. Bifilar magnet wires which have been dip coated with a polyimide or other polymer to form an insulating coating are useful for this purpose, because they have a narrower diameter than wound wire. The wires are run through the length of the catheter to their termination point in the tip structure as described above. In a particularly preferred embodiment of the present invention, the wires are surrounded by a support tube 26 (FIGS. 2 and 3) at the distal end of the catheter and which terminates in the tip structure as shown in FIGS. 2 and 3. Support tube 26 serves several functions. The space between the outside wall of support tube 26 and the inside wall of the catheter 10 provides a passage 40 through which saline or other fluid can be introduced into the tip structure. Support tube 26 also provides additional stiffness to catheter 10. Support tube 26 is preferably glued and/or pinned to the catheter in one or more places to immobilize it to the catheter and prevent its movement within the catheter.

The present device also preferably includes a shock-absorbing resilient material 48 (FIG. 3) disposed between the catheter 10 and the piston 30. This resilient material 48 absorbs vibration created by the return of the piston to its' original position and prevents such vibration from being transmitted along the catheter. A nylon bushing is particularly useful for this purpose, however, other resilient, shock-absorbing materials can be used. The shock-absorbing material 48 is preferably disposed adjacent a stop member 50 which member is positioned to prevent the rearward travel of piston 30 beyond distance D1 from the electrodes 28.

Figure 4A:
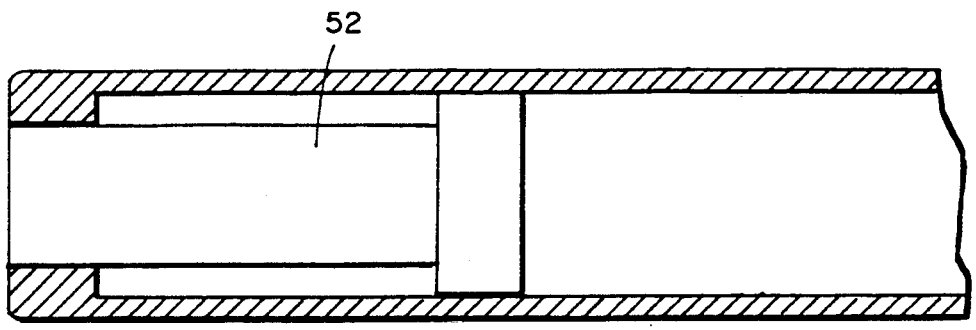
FIG. 4 is a schematic cross-sectional view of the tip structure containing (A) a scraping implement, (B) a cutting implement, or (c) a wedge driving implement.
Figure 4B:
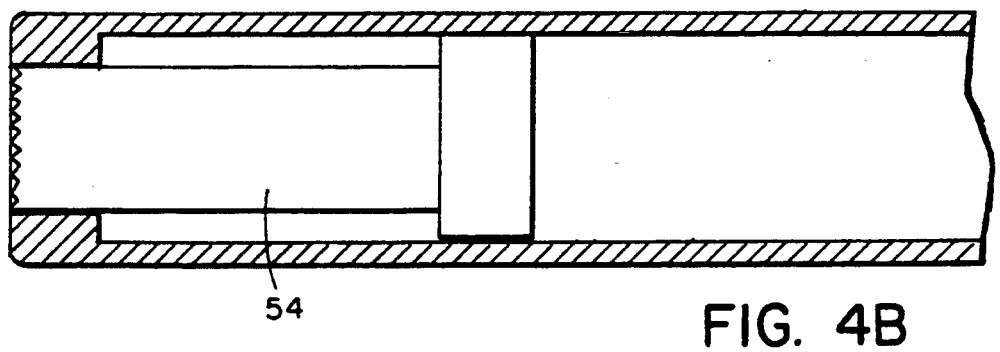
Figure 4C:
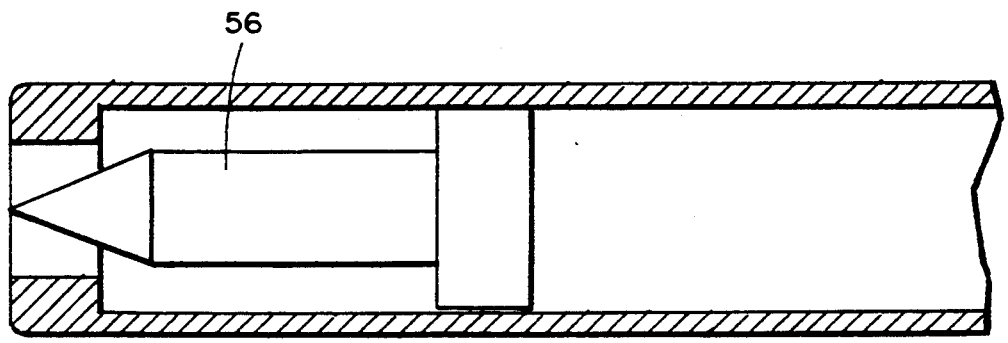

FIGS. 4A, 4B and 4C illustrate further versions of the embodiments of FIGS. 1, 2 and 3. FIG. 4A shows a scraping implement 52 in lieu of the piston 30. FIG. 4B illustrates the present catheter and tip structure equipped with a cutting blade 54 in lieu of the piston 30. FIG. 4C illustrates a driving wedge or splitting implement 56.

In operation, a catheter 10 according to the present invention is inserted through a body passage such as the urethra, for kidney stone fracturing, the biliary duct for gall stone fracturing or an artery for arterial plaque break-up. The tip 12 can be guided by fluoroscopy or an X-ray source and viewing display which permit the tip structure to be guided to a position adjacent a deposit to be treated. Fluid is provided to the tip structure through passage 40, or may be admitted from the surrounding environment through ports 44. Once the tip is in the proper position and is supplied with fluid, energy is applied from the power source. If the power source is a laser, then a pulsed laser beam is transmitted through conduit 24, which is an optical fiber, to the tip structure, where it causes repeated vaporizations of the fluid. If a spark generator is used as the power source, a series of sparks from electrodes 28 causes repeated vaporizations of fluid within shielded region 22 of housing 16. The vaporizations form cavitation bubbles which expand and cause pressure to be applied to driving surface 32. This pressure causes the piston 30 to move forward, and impact end 16 to project beyond distal end 20 of the housing, and contact the target deposit. This motion causes compression of spring means 38. The piston element 30 is prevented from leaving housing 16 by the shoulders 34, spring 38 and spring stops 18. The spring 38 causes the piston to return to its original position.

The design of the present catheter permits repeated impacts to be made against the deposit. The narrower diameter catheter means that the catheter is minimally invasive, and can be used in smaller body passages. The impact element can be replaced by scraping, cutting or splitting implements or can be adapted for other tools designed for microsurgery.

EQUIVALENTS

Those skilled in the art will recognize, or be able to ascertain, using no more than routine experimentation, numerous equivalents to the specific embodiments described herein. Such equivalents are considered to be within the scope of this invention, and are covered by the following claims.

We claim:

1. A device for impacting a formation in a body passage comprising:
   an elongate flexible member for insertion into a body passage;
   a housing defining a proximal end and a distal end, the proximal end of said housing being coupled to the elongate flexible member such that, in an operative position, the housing is located within the body passage;
   a pair of electrodes located within said housing and defining a spark gap disposed within said housing wherein the electrodes are disposed within a tube which is attached to an inner wall of the housing;
   a piston, defining an impact element extendable beyond the distal end of said housing, said piston being mounted within said housing such that, in response to a spark being generated across said spark gap, said piston moves axially within said housing away from a rest position so that the impact element moves away from the distal end of said housing; and
   a spring located within the housing, the spring being located between the piston and the housing, wherein the spring is biased to return said piston to said rest position after a discharge from said electrodes has driven said piston away from said rest position.

2. The device of claim 1 wherein the electrodes are chamfered.

3. The device of claim 2 wherein the spark gap is about 0.015 inches to about 0.030 inches.

4. The device of claim 1 wherein the piston defines a driving surface located about 0.040 inches ±0.010 inches from the electrodes when the piston is in a first position prior to the generation of a spark across said spark gap.

5. The device of claim 1 further comprising means for introducing liquid into the housing.

6. The device of claim 5 wherein the housing further comprises ports near the distal end.

7. A device for impacting a formation within a body passage comprising:
   an elongate flexible member for insertion into the body passage;
   a housing defining a proximal end and a distal end, the proximal end of said housing being coupled to the elongate flexible member such that, in an operative position, the housing is located within the body passage;
   a pair of electrodes located within said housing and defining a spark gap disposed within said housing;
   means for introducing liquid into the housing;
   a piston, defining an impact element extendable beyond the distal end of said housing, said piston being mounted for axial reciprocating movement within said housing such that, in response to a spark being generated across said spark gap, said piston moves axially within said housing away from the distal end of said housing, wherein the piston includes a central lumen and a port formed in a distal portion of the piston to permit the passage of liquid through the piston; and
   a shock absorbing element disposed between said piston and said elongate flexible member for inhibiting transmission of vibrations along said flexible member.

8. The device of claim 7 wherein the electrodes are chamfered.

9. The device of claim 8 wherein the spark gap is about 0.015 inches to about 0.030 inches.

10. The device of claim 7 wherein the piston defines a driving surface located about 0.040 inches ±0.010 inches from the electrodes when the piston is in a first position prior to the generation of a spark across said spark gap.

11. The device of claim 7 further comprising a spring mounted within said housing and abutting a surface of said piston.

12. The device of claim 7 wherein the housing further comprises ports near the distal end.

13. The of device claim 7 wherein the impact element includes a blunt surface for impacting and fracturing a hard formation in a body passage.

14. The device of claim 7 wherein the impact element includes a scraping implement.

15. The device of claim 7 wherein the impact element includes a cutting implement.

16. A device for impacting a formation in a body passage comprising:
   an elongate flexible member for insertion into a body passage;
   a housing defining a proximal end and a distal end, the proximal end of said housing being coupled to the elongate flexible member such that, in an operative position, the housing is located within the body passage;
   a pair of electrodes located within said housing and defining a spark gap disposed within said housing;
   a piston, defining an impact element and a driving surface, said piston being mounted for axial reciprocating movement between a rest position and a formation contact position, said piston being mounted in said housing such that, upon a discharge from said electrodes, said piston is driven from said rest position into said formation contact position, and wherein said driving surface is disposed adjacent to said pair of electrodes when said piston is in said rest position, wherein the piston includes a central lumen and a port formed in a distal portion of the piston to permit the passage of liquid through the piston;
   means for introducing liquid into the housing; and
   a spring disposed within the housing, the spring being located between the piston and the housing, wherein the spring is biased to return said piston to said rest position after a discharge from said electrodes has driven the piston into said formation contact position.

17. The device of claim 16 wherein the electrodes are chamfered.

18. The device of claim 17 wherein the spark gap is about 0.010 inches to 0.030 inches.

19. The device of claim 16 wherein the distance between the driving surface of the piston and the electrodes is between about 0.030 inches to about 0.080 inches when the piston is located in the rest position.

20. The catheter of claim 16 wherein the housing further comprises ports near the distal end.

21. A device for impacting a formation in a body passage comprising:
   an elongate flexible member for insertion into a body passage;
   a cylindrical housing, comprising a proximal end and a distal end, the proximal end of the housing being attached to a distal end of the flexible member such that, in an operative position, the housing is located within the body passage, the housing forming an extension of the flexible member and defining an opening at a distal end thereof;
   a pair of electrodes defining a spark gap disposed within a tube which is attached to an inner surface of the housing;
   means for introducing liquid into the housing;
   a retractable probe having an impact end including a cutting surface and a driving end, the probe being mounted for reciprocal movement within the housing such that, upon the generation of a spark across the spark gap, the probe moves axially away from a retracted position so that the cutting surface extends from the distal end of the housing; and
   means for returning the probe to the retracted position.

22. The device of claim 21 wherein the electrodes are chamfered.

23. The device of claim 22 wherein the spark gap is about 0.015 inches to about 0.030 inches.

24. The device of claim 21 wherein the housing further comprises ports near the distal end.

25. The device of claim 21 wherein the distance between a driving end of the probe and the electrodes is about 0.040 inches ±0.010 inches when the probe is located in the retracted position.

26. The device of claim 21 further comprising a shock absorbing means disposed between the probe and the flexible member.

27. The device of claim 21 wherein the probe further defines a central lumen and ports near the probe tip.

28. The device of claim 21 wherein the probe comprises a wedge-shaped splitting instrument.

* * * * *